United States Patent [19]

Johnson

[11] Patent Number: 5,312,438
[45] Date of Patent: May 17, 1994

[54] SUTURE ANCHOR AND METHOD OF USE

[75] Inventor: Lanny L. Johnson, 4528 Hagadorn, East Lansing, Mich. 48823

[73] Assignee: Lanny L. Johnson, Okemos, Mich.

[21] Appl. No.: 55,310

[22] Filed: May 3, 1993

[51] Int. Cl.⁵ .............................................. A61B 17/00
[52] U.S. Cl. ..................................... 606/232; 606/72; 606/104
[58] Field of Search ................. 606/232, 72, 104, 139; 623/13; 411/508, 509, 510, 512, 340

[56] References Cited

U.S. PATENT DOCUMENTS

| | | | |
|---|---|---|---|
| 4,738,255 | 4/1988 | Goble et al. | 606/232 |
| 4,898,156 | 2/1990 | Gatturna et al. | 606/232 |
| 4,968,315 | 11/1990 | Gatturna | 606/72 |
| 5,100,417 | 3/1992 | Cerier et al. | 606/232 |
| 5,224,946 | 7/1993 | Hayhurst et al. | 606/232 |

OTHER PUBLICATIONS

Orthopedics Today, Jul. 1992, pp. 1, 14 and 15.
Plagens Ortho Paper (date unknown), describing Mitek Suture Anchors.
Acufex Microsurgical, Inc. brochure (date unknown) describing Suretac fixation device.

*Primary Examiner*—Stephen C. Pellegrino
*Assistant Examiner*—Gary Jackson

[57] ABSTRACT

A suture anchor is disclosed which comprises a frusto-conical device having first and second axial ends, and a side surface extending therebetween. The first axial end has a larger diameter than the second axial end. The first axial end includes an internally threaded bore by which a driver is removably connected to the anchor. A passage extends through the suture anchor from the second axial end and to the side surface. Tissue is attached to a bone by first passing a length of suture material through the tissue. The suture ends are delivered to the anchor and are passed through the passage in a direction from the axial end to the side surface. The user then grasps the suture ends and inserts the anchor, by means of the driver, into a previously prepared bore in the bone. The anchor is wedged into the bore so that the suture is captured between the bone and the side surface of the anchor.

13 Claims, 3 Drawing Sheets

SUTURE ANCHOR AND METHOD OF USE

BACKGROUND AND SUMMARY OF THE INVENTION

1. Field of the Invention

The present invention relates to suture anchors and, in particular, to anchors having a substantially frusto-conical shape and a passage within the anchor to allow strands of suture to pass through the anchor between an end and the side surface thereof.

2. Description of the Art

Currently, most suture anchors that are used in the medical field are of the type that have tissue attached to an anchor which is embedded in bone. Typically, a suture is secured to an anchor which is affixed to the bone, and the suture is used to tie tissue to the bone. A problem with such conventional suture anchors is that it often is difficult to attach tissue, such as ligaments and tendons, to a bone at a desired location because of difficulties in securing an anchor to bone at the optimum site for the surgical repair being performed. Accordingly, there is a need for a suture anchor which is easy to use and which allows the surgeon to attach tissue to a bone in a relatively inaccessible location.

To that end, the present invention relates to a suture anchor having a generally frusto-conical configuration with a passage extending from the smaller diameter base of the anchor to an opening on the side thereof. The side of the anchor can be a smooth surface, or alternatively, it can be corrugated. When suture is inserted in the passage through the anchor and the anchor is forced into a bore provided in the bone, the suture is wedged between the side of the anchor and the sidewall of the bore. If the bore passes all the way through the bone, and the suture is introduced to the anchor from the side of the bone opposite that to which the anchor is embedded, tissue can be secured to the bone at a site separated from the location of the suture anchor.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings, all of which form a part of this specification, wherein like reference numerals designate corresponding parts in the various figures.

DETAILED DESCRIPTION OF THE INVENTION

Figure 1:
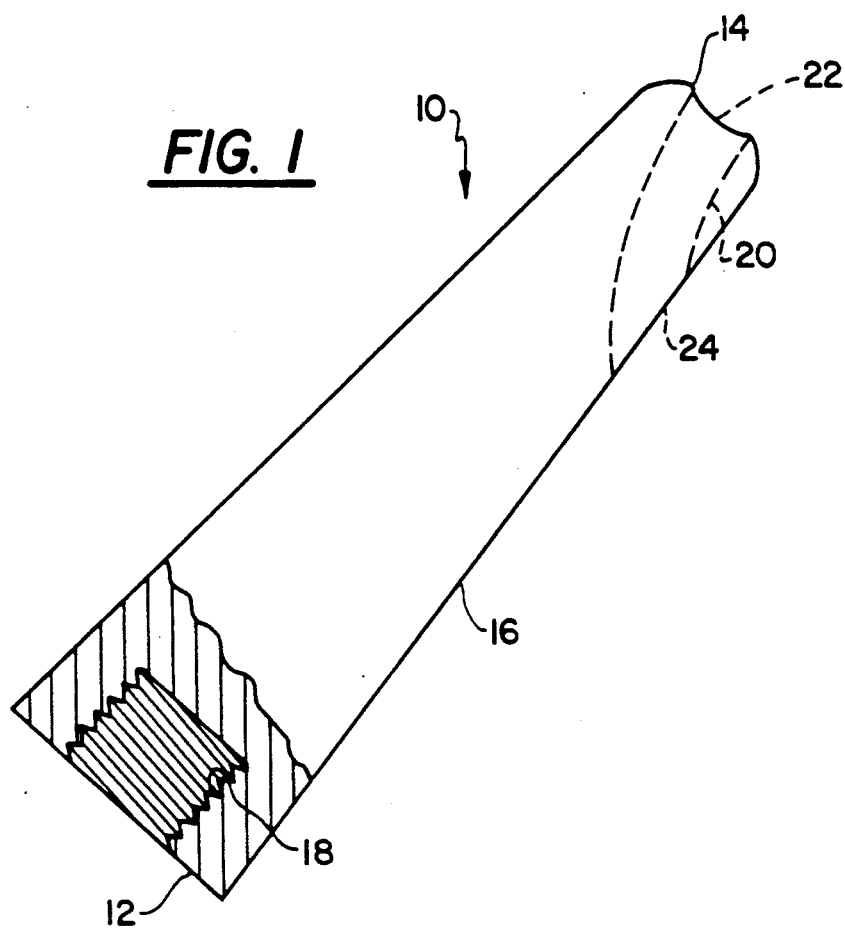
FIG. 1 is a perspective view, partially in section, of a first embodiment of a suture anchor in accordance with the present invention.
Figure 2:
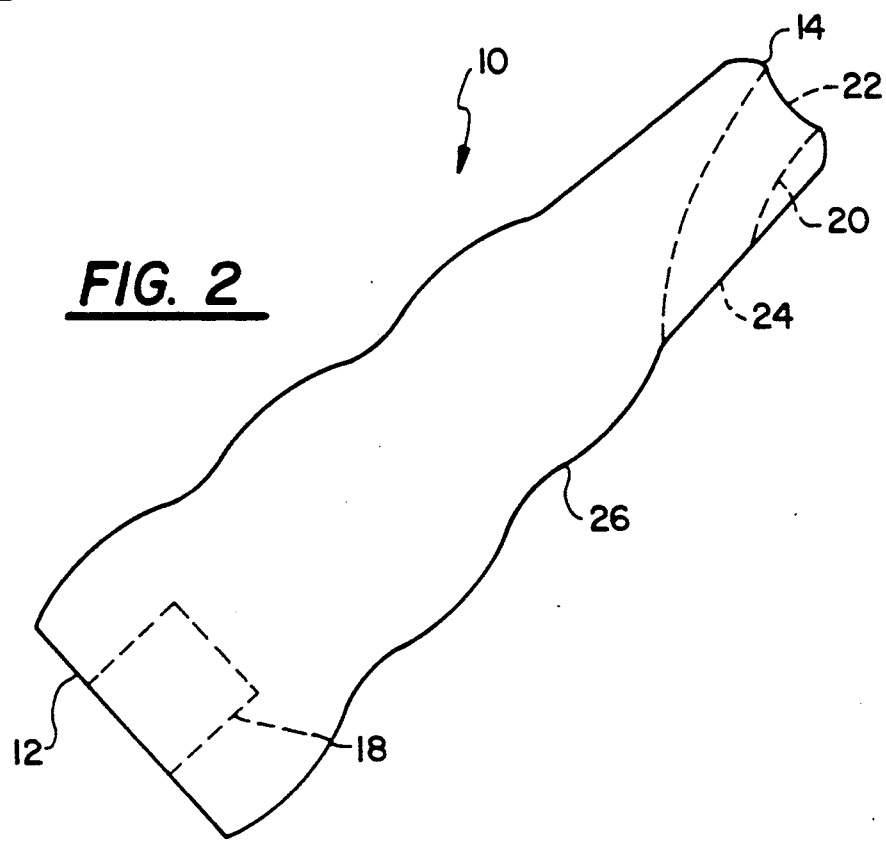
FIG. 2 is a perspective view of a second embodiment thereof.

Referring now to the drawings, FIGS. 1 and 2 illustrate a suture anchor 10 having a substantially frusto-conical configuration. The anchor is formed from metals or plastic material customary utilized for surgical applications.

Anchor 10 includes a first axial end 12, a second axial end 14 and a wedge-shaped side 16. The first axial end 12 has a larger diameter than the second axial end 14. An internally threaded bore 18 is provided at end 12, and a passage 20 is formed within anchor 10. The passage extends between an opening 22 at end 14 of the anchor 10 and an opening 24 in the side 16 of the anchor adjacent end 14. For a typical application, the anchor is about 13 mm in length, axial ends 12 and 14 are approximately 4 and 2 mm in diameter, respectively, and the passage 20 is about 1 mm wide. Of course, other dimensions are contemplated, depending on the particular application for the anchor.

So as not to cut the suture material, sharp edges at axial end 14 of the anchor, and at the ends of the passage 20 therethrough, are rounded.

In the embodiment shown in FIG. 1, the surface of side 16 is smooth. However, as illustrated in FIG. 2, the surface 16 can be corrugated or undulating, rather than smooth.

The method by which a suture anchor of the type shown in FIGS. 1 and 2 is deployed now will be described with reference to FIGS. 3-5.

Figure 3:
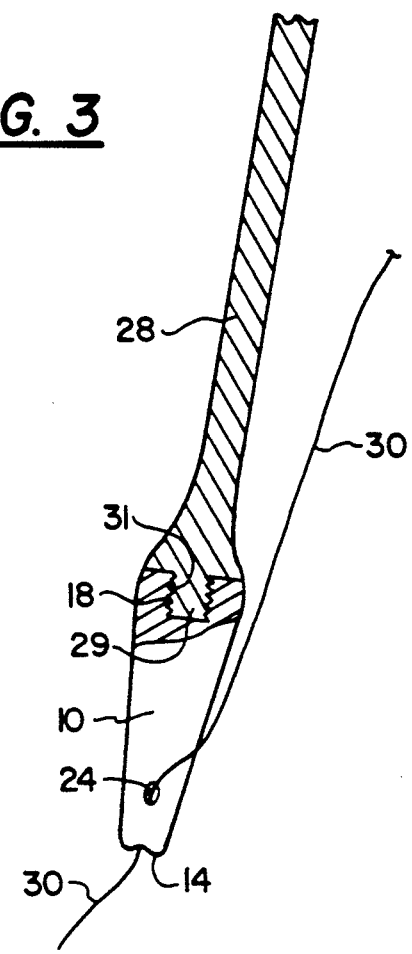
FIG. 3 is a perspective view illustrating a suture anchor, a driver therefor, and a loop of suture material passing through the suture anchor.
Figure 4:
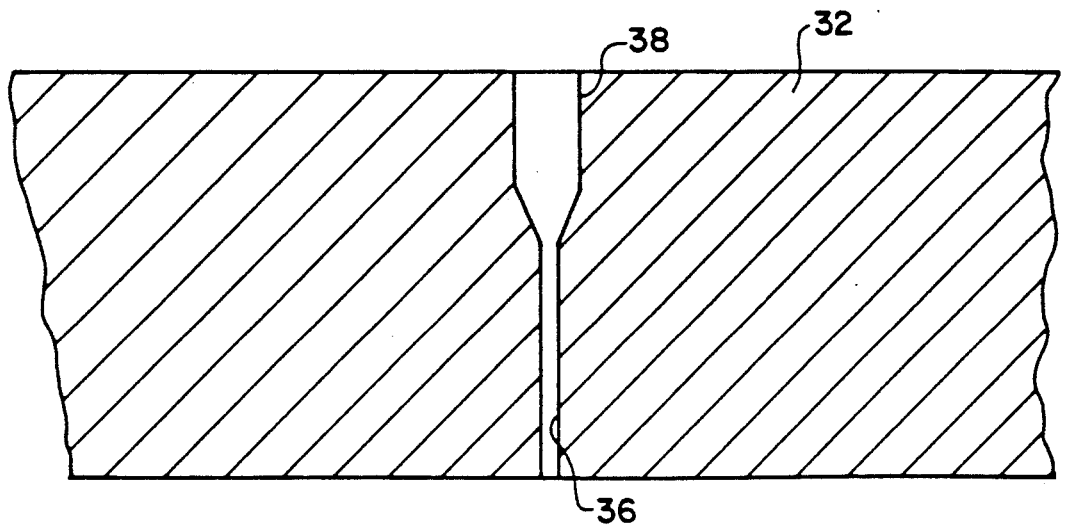
FIG. 4 is a cross-sectional view of a bone showing a bore arrangement provided therein for receiving suture and a suture anchor.

FIG. 3 illustrates a driver 28 which is connected to the anchor 10 using the threaded bore 18. The driver 28 includes an axially projecting end portion 29 that includes male threads 31 which are sized to mate with the internally threaded bore 18 in the anchor.

As will be described in greater detail hereinafter, the driver 28 is used to place anchor 10 within a predrilled hole or bore in a bone. The manner in which the bone is drilled is shown in FIG. 4. More particularly, FIG. 4 illustrates a bone 32 prepared for a surgical procedure wherein tissue is to be secured to the bone at a location where affixing a suture anchor to the bone would be difficult. A hole 36 is drilled completely through the bone. On the side of the bone proximal the surgeon's access to the bone, the hole 36 is countersunk to a depth sufficient to receive an anchor 10. The diameter of the countersunk bore 38 is greater than that of the axial end 14 of the anchor but less than that of axial end 12. This relative sizing allows the suture anchor 10 to be fixed to the bone by being compressed within bore 38.

Figure 5:
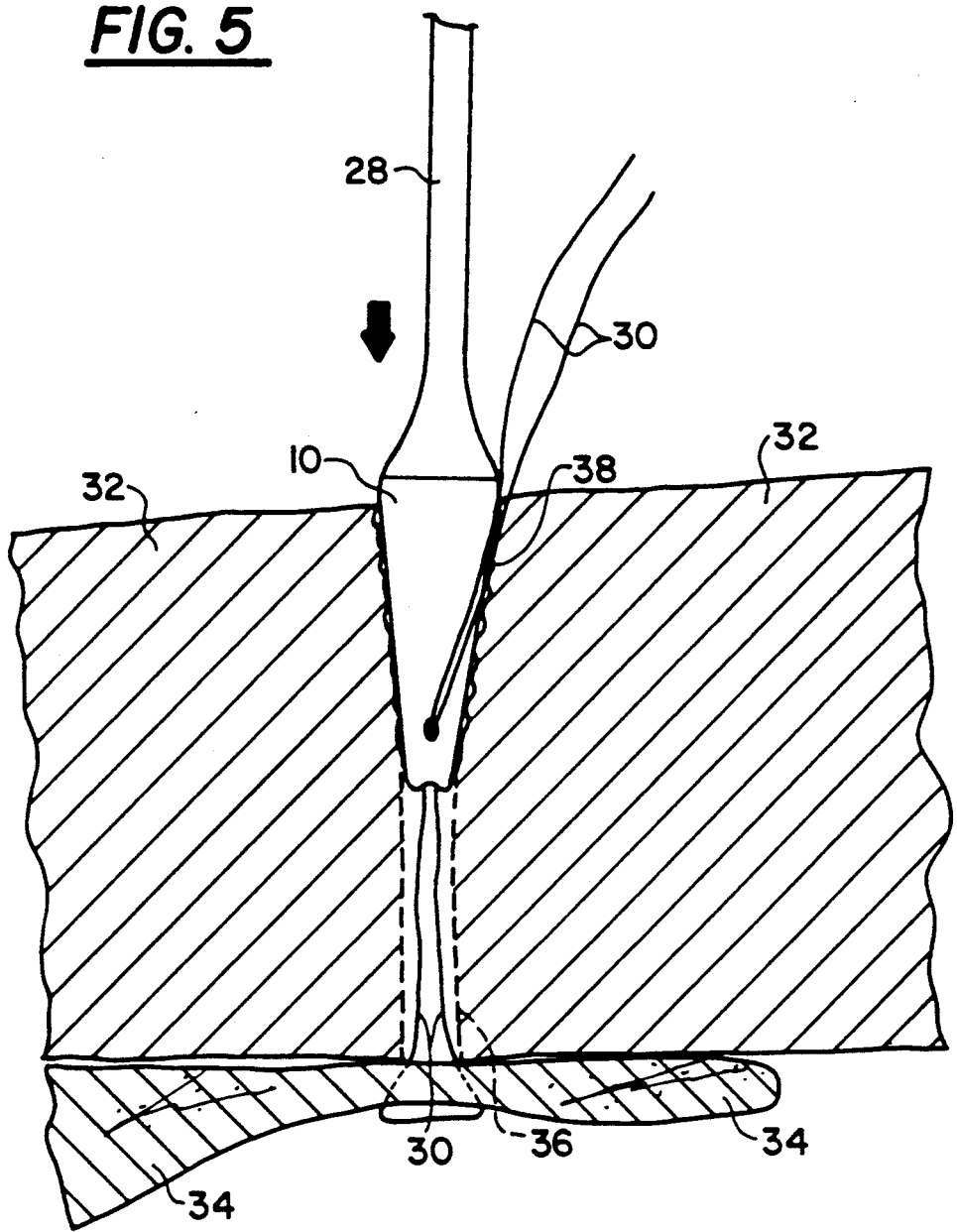
FIG. 5 is a diagrammatic view illustrating the method of embedding a suture anchor in bone and securing tissue to the bone by means of suture passing through the tissue and the anchor.

Referring now to FIG. 5, a loop of suture material is placed in the tissue 34 which is to be secured to bone 32. The two ends 30 of the suture are passed through the predrilled hole 36 and bore 38 in the bone and then through a cannula (not shown) previously positioned with an end adjacent bore 38. The cannula directs the suture ends to the surgeon who has prepared a suture anchor 10 for delivery to the surgical site by connecting it to the driver 28 in the manner previously described.

The surgeon threads the ends of the suture through the passage 20, the suture entering the anchor at axial end 14 and exiting from the opening 24 located on the side of the anchor. The surgeon then grasps the suture ends and draws the tissue 34 against the bone 32. Simultaneously, the anchor and connected driver 28 are slid down the cannula until the narrower end 14 of the anchor enters the countersunk bore 38 in the bone.

When the tissue is secured against the opposite side of the bone to the surgeon's satisfaction, the anchor 10 is wedged into bore 38, by force exerted on the driver 28, so that the suture ends are loosely restrained between the bone 32 and the side surface 16 of the anchor. The surgeon then rechecks to determine whether the tissue is firmly held to the bone. If it is not, the suture ends are pulled to further draw the tissue against the bone. When the tissue 34 is properly secured, the suture anchor is forced further into place within bore 38 for final fixation of the anchor. The driver 28 is then separated from the suture anchor 10 and withdrawn from the surgical site. The suture ends can be cut adjacent the axial end 12 of the embedded anchor, or a knot can be tied in the suture over end 12 to deter the anchor from being pulled out of the bore 38 in the bone.

The invention may be used in a wide variety of applications. It is especially useful in securing ligaments relative to synovial joints in treating such things such as glenohumeral instability and rotation cuff tears, as well as performing knee and ankle ligament repairs.

While the foregoing description relates to anchoring suture on the opposite side of a bone from the location where the suture secures tissue to the bone, it will be apparent that the anchor which has been disclosed also can be used to retain suture in applications where the tissue is tied to the bone proximate the anchor.

The invention has been described in connection with what is presently considered to be the most practical and preferred embodiment. However, it is to be understood that the invention is not limited to the disclosed embodiment, but, on the contrary, is intended to cover various modifications and equivalent arrangements included within the spirit and scope of the appended claims.

What is claimed is:

1. A suture anchor comprising:
   (a) a substantially frusto-conical device having first and second axial ends and a side surface extending therebetween, said first axial end having a diameter larger than said second axial end; and
   (b) a passage within said device for allowing suture to be threaded therethrough, said passage extending from said second axial end to said side surface.

2. A suture anchor according to claim 1, wherein said passage opens on said side surface closer to said second axial end than to said first axial end.

3. A suture anchor according to claims 1 or 2, wherein said side surface is corrugated.

4. A suture anchor according to claim 3, wherein a bore is provided within said first axial end for receiving driver means for embedding said anchor in bone.

5. A suture anchor according to claim 4, wherein said bore is internally threaded.

6. A suture anchor according to claims 1 or 2, wherein a bore is provided within said first axial end for receiving driver means for embedding said anchor in bone.

7. A suture anchor according to claim 6, wherein said bore is internally threaded.

8. A suture anchor according to claim 6, wherein said side surface is corrugated.

9. A method of anchoring suture to a bone so that tissue may be secured to the bone by the suture, comprising the steps of:
   (a) passing a length of suture through the tissue;
   (b) delivering the ends of the suture to a suture anchor of the type comprising:
      (1) a substantially frusto-conical device having first and second axial ends and a side surface extending therebetween, said first axial end having a diameter larger than said second axial end; and
      (2) a passage within said device for allowing suture to be threaded therethrough, said passage extending from said second axial end to said side surface;
   (c) threading the suture ends through said passage in a direction from the second axial end of the device towards said side surface;
   (d) grasping the suture ends and applying tension thereto to draw the tissue against said bone;
   (e) inserting the suture anchor, second axial end first, into a bore in said bone, the bore having a diameter greater than that of the second axial end and less than that of said first axial end; and
   (f) forcing the anchor into the bore until the suture is captured between the bone and the side surface of the suture anchor.

10. A method according to claim 9, wherein the tissue is located on an opposite side of the bone from the bore into which the anchor is inserted, said suture ends being delivered to the suture anchor through a hole in the bone which is coaxial with said bore.

11. A method according to claims 9 or 10, further comprising the step of cutting the suture ends proximate said first axial end of the anchor after said suture has been captured.

12. A method according to claims 9 or 10, further comprising the step of tying a knot in the suture ends proximate the first axial end of the anchor after said suture has been captured.

13. A method according to claims 9 or 10, wherein the suture anchor is inserted and forced into the bore by a driver adapted to be removably secured to said first axial end of the anchor.

* * * * *